(12) United States Patent
Watanabe et al.

(10) Patent No.: US 9,334,233 B2
(45) Date of Patent: May 10, 2016

(54) METHOD FOR PRODUCING ACRYLONITRILE

(71) Applicant: Mitsubishi Rayon Co., Ltd., Chiyoda-ku (JP)

(72) Inventors: Hirokazu Watanabe, Otake (JP); Motoo Yanagita, Yokohama (JP); Takashi Karasuda, Yokohama (JP); Kazufumi Nishida, Otake (JP); Kenichi Miyaki, Otake (JP)

(73) Assignee: Mitsubishi Rayon Co., Ltd., Chiyoda-ku (JP)

( * ) Notice: Subject to any disclaimer, the term of this patent is extended or adjusted under 35 U.S.C. 154(b) by 0 days.

(21) Appl. No.: 14/381,002

(22) PCT Filed: Feb. 26, 2013

(86) PCT No.: PCT/JP2013/054871
§ 371 (c)(1),
(2) Date: Aug. 26, 2014

(87) PCT Pub. No.: WO2013/129363
PCT Pub. Date: Sep. 6, 2013

(65) Prior Publication Data
US 2015/0065744 A1 Mar. 5, 2015

(30) Foreign Application Priority Data
Feb. 29, 2012 (JP) .................................. 2012-042831

(51) Int. Cl.
C07C 253/26 (2006.01)
B01J 23/889 (2006.01)
B01J 35/00 (2006.01)

(52) U.S. Cl.
CPC ........... *C07C 253/26* (2013.01); *B01J 23/8898* (2013.01); *B01J 35/002* (2013.01); *B01J 2523/00* (2013.01)

(58) Field of Classification Search
CPC .................................................... C07C 253/26
See application file for complete search history.

(56) References Cited

U.S. PATENT DOCUMENTS

| | | |
|---|---|---|
| 2,904,580 A | 9/1959 | Idol, Jr. et al. |
| 3,044,960 A | 7/1962 | Morway et al. |
| 3,056,546 A | 10/1962 | Zenner |
| 3,248,340 A | 4/1966 | Callahan et al. |
| 3,472,892 A | 10/1969 | Callahan |
| 3,746,657 A | 7/1973 | Miller et al. |
| 3,882,159 A | 5/1975 | Callahan et al. |
| 4,536,483 A | 8/1985 | Sasaki et al. |
| 5,132,269 A | 7/1992 | Sasaki et al. |
| 5,177,048 A | 1/1993 | Chen et al. |
| 5,378,668 A | 1/1995 | Beuke et al. |
| 6,084,119 A | 7/2000 | Midorikawa |
| 6,653,496 B1 | 11/2003 | Mori et al. |
| 6,723,869 B1 | 4/2004 | Mori |
| 7,576,232 B2 | 8/2009 | Seely |
| 8,034,737 B2 | 10/2011 | Watanabe |

FOREIGN PATENT DOCUMENTS

| | | | |
|---|---|---|---|
| DE | 33 11 521 | 1/1984 | |
| EP | 0 889 027 A1 | 1/1999 | |
| JP | 36-5870 | 5/1961 | |
| JP | 37-8568 | 7/1962 | |
| JP | 38-17967 | 9/1963 | |
| JP | 51-33888 | 9/1976 | |
| JP | 54-12913 | 5/1979 | |
| JP | 57-49253 | 10/1982 | |
| JP | 58-57422 | 12/1983 | |
| JP | 59-76543 | 5/1984 | |
| JP | 59-76544 | 5/1984 | |
| JP | 4-118051 | 4/1992 | |
| JP | 4-227072 | 8/1992 | |
| JP | 5-301051 | 11/1993 | |
| JP | 6-9530 | 1/1994 | |
| JP | 07-289901 | 11/1995 | |
| JP | 11-33400 | 2/1999 | |
| JP | 2001-018772 | 1/2001 | |
| JP | 2001-114740 | * 4/2001 | ............ C07C 253/26 |
| JP | 2001-187772 | 7/2001 | |
| JP | 2002-306968 | 10/2002 | |

(Continued)

OTHER PUBLICATIONS

International Search Report issued May 14, 2013 in PCT/JP13/054871, filed Feb. 26, 2013.
Third Party Observation, Communication Pursuant to Rule 114(2) EPC, in corresponding European Patent Application No. 13755100.8.
Robert K, Grasselli, "Advances and Future Trends in Selective Oxidation and Ammoxidation Catalysis", Catalysis Today, vol. 49, No. 1-03, Feb. 1, 1999, pp. 141-153, XP000944840, DOI:10.1016/SO920-5861(98)00418-0.

*Primary Examiner* — Joseph Kosack
(74) *Attorney, Agent, or Firm* — Oblon, McClelland, Maier & Neustadt, L.L.P.

(57) ABSTRACT

The invention relates to a method for producing acrylonitrile which includes a vapor phase catalytic ammoxidation process of performing vapor phase catalytic ammoxidation by bringing a source gas containing propylene, molecular oxygen, and ammonia into contact with a fluidized bed catalyst to obtain acrylonitrile. The method is characterized in that the fluidized bed catalyst is a catalyst containing molybdenum and bismuth and the vapor phase catalytic ammoxidation process is performed while maintaining an adsorbed amount of ammonia per specific surface area ($m^2/g$) of the fluidized bed catalyst in the range of 0.05 to 0.6 $\mu mol/m^2$. According to the method for producing acrylonitrile of the invention, it is possible to stably maintain a high acrylonitrile yield over a long period of time.

5 Claims, No Drawings

(56) References Cited

FOREIGN PATENT DOCUMENTS

| JP | 2005-162707 | 6/2005 |
| JP | 2009-285581 | 12/2009 |
| JP | 2010-172851 | 8/2010 |
| WO | 97/33868 | 9/1997 |

* cited by examiner

METHOD FOR PRODUCING ACRYLONITRILE

TECHNICAL FIELD

The present invention relates to a method for producing acrylonitrile by vapor phase catalytic ammoxidation of propylene by molecular oxygen and ammonia.

This application claims priority based on Japanese Patent Application No. 2012-042831 filed on Feb. 29, 2012, the entire contents of which are incorporated herein by reference.

BACKGROUND ART

A method is widely known in which acrylonitrile is produced by a vapor phase catalytic ammoxidation reaction using propylene, ammonia, and molecular oxygen (oxygen-containing gas) as a starting material in a fluidized bed reactor. In particular, a composite oxide catalyst containing molybdenum and bismuth is useful in the ammoxidation reaction and thus industrially widely used.

Hitherto, a large number of researches have been made on the composite oxide catalyst containing molybdenum and bismuth and various catalysts have been proposed.

For example, a catalyst containing molybdenum and bismuth is disclosed in Patent Document 1. In addition, a catalyst containing molybdenum, bismuth, and iron is disclosed in Patent Document 2. Moreover, a catalyst further containing other components in addition to molybdenum and bismuth is disclosed in Patent Documents 3 to 6.

In addition, a method for producing a composite oxide catalyst containing molybdenum and bismuth is disclosed in Patent Documents 7 to 9.

However, the ammoxidation reaction is typically carried out at a high temperature of 400 to 500° C. For that reason, the molybdenum component or the like in the catalyst is easily volatilized and thus the catalyst performance tends to decrease time dependently.

Therefore, as a countermeasure, a method is disclosed in, for example, Patent Document 10 in which molybdenum oxide is supported on an inert support and this is reacted by mixing with a catalyst. In addition, a method is disclosed in Patent Document 11 in which a reactivating agent containing molybdenum, phosphorus, chromium, bismuth, and the like is added to the catalyst. Moreover, a method using a molybdenum-enriched catalyst is disclosed in Patent Documents 12 to 15. Furthermore, a method is disclosed in Patent Documents 16 to 18 in which the reaction is performed while adding a molybdenum-containing compound which is not supported on a support.

CITATION LIST

Patent Document

Patent Document 1: JP 36-5870 B
Patent Document 2: JP 38-17967 B
Patent Document 3: JP 51-33888 B
Patent Document 4: JP 6-9530 A
Patent Document 5: JP 7-289901 A
Patent Document 6: JP 4-118051 A
Patent Document 7: JP 37-8568 B
Patent Document 8: JP 57-49253 B
Patent Document 9: JP 54-12913 B
Patent Document 10: JP 58-57422 B
Patent Document 11: JP 4-227072 A
Patent Document 12: U.S. Pat. No. 5,177,048
Patent Document 13: JP 5-301051 A
Patent Document 14: JP 59-76544 A
Patent Document 15: JP 11-33400 A
Patent Document 16: DE 3,311,521
Patent Document 17 WO 97/33868 A
Patent Document 18: JP 59-76543 A

DISCLOSURE OF THE INVENTION

Problem to be Solved by the Invention

However, the catalyst or the method for producing thereof disclosed in these prior arts and the method for producing acrylonitrile exhibit an effect of maintaining a high acrylonitrile yield to some extent but the effect is not always sufficient. Accordingly, it is desired a method for producing acrylonitrile at a higher yield.

In addition, there is a concern that an additive such as molybdenum is added in excess in the prior art, and in this case, molybdenum or the like may be volatilized from the additive added in excess and attached to the apparatus for producing acrylonitrile, as a result, it is difficult to produce acrylonitrile stably over a long period of time in some cases.

The invention has been made in view of the above circumstances, and an object thereof is to provide a method for producing acrylonitrile capable of stably maintaining a high acrylonitrile yield over a long period of time.

Means for Solving Problem

An aspect of the method for producing acrylonitrile of the invention is a method for producing acrylonitrile by the vapor phase catalytic ammoxidation of propylene by molecular oxygen and ammonia in a fluidized bed reactor using a fluidized bed catalyst containing molybdenum and bismuth. The method is characterized in that the vapor phase catalytic ammoxidation reaction is performed while maintaining an adsorbed amount of ammonia per specific surface area ($m^2/g$) of the fluidized bed catalyst during the vapor phase catalytic ammoxidation reaction in the range of 0.05 to 0.6 $\mu mol/m^2$.

In addition, it is preferable that the fluidized bed catalyst be represented by the following Formula (1).

$$Mo_{12}Bi_aFe_bA_cD_dE_eG_fO_x(SiO_2)_y \qquad (1)$$

In Formula (1), Mo, Bi, Fe, O, and $SiO_2$ represent molybdenum, bismuth, iron, oxygen, and silica, respectively, A represents at least one kind of element selected from the group consisting of nickel, cobalt, zinc, magnesium, manganese, and copper, D represents at least one kind of element selected from the group consisting of lanthanum, cerium, praseodymium, neodymium, and samarium, E represents at least one kind of element selected from the group consisting of lithium, sodium, potassium, rubidium, and cesium, G represents at least one kind of element selected from the group consisting of calcium, strontium, barium, cadmium, titanium, zirconium, vanadium, niobium, tantalum, chromium, tungsten, germanium, tin, yttrium, aluminum, gallium, ruthenium, rhodium, palladium, rhenium, osmium, iridium, platinum, silver, boron, phosphorus, antimony, and tellurium, and a, b, c, d, e, f, x, and y represent an atomic ratio, a is 0.1 to 5, b is 0.1 to 10, c is 2 to 12, d is 0.01 to 5, e is 0.01 to 2, f is 0 to 10, y is 20 to 200, and x is the number of oxygen atom required to satisfy the valence of each of the components except silica.

In addition, the method for producing acrylonitrile of the invention has the following aspects.

<1> A method for producing acrylonitrile, the method including a vapor phase catalytic ammoxidation process of performing vapor phase catalytic ammoxidation by bringing a source gas containing propylene, molecular oxygen, and ammonia into contact with a fluidized bed catalyst to obtain acrylonitrile, in which the fluidized bed catalyst is a catalyst containing molybdenum and bismuth, and the vapor phase catalytic ammoxidation process is performed while maintaining an adsorbed amount of ammonia per specific surface area ($m^2/g$) of the fluidized bed catalyst in the range of 0.05 to 0.6 $\mu mol/m^2$;

<2> The method for producing acrylonitrile according to <1>, in which the fluidized bed catalyst is represented by the following Formula (1);

$$Mo_{12}Bi_aFe_bA_cD_dE_eG_fO_x \cdot (SiO_2)_y \qquad (1)$$

(in Formula (1), Mo, Bi, Fe, O, and $SiO_2$ represent molybdenum, bismuth, iron, oxygen, and silica, respectively, A represents at least one kind of element selected from the group consisting of nickel, cobalt, zinc, magnesium, manganese, and copper, D represents at least one kind of element selected from the group consisting of lanthanum, cerium, praseodymium, neodymium, and samarium, E represents at least one kind of element selected from the group consisting of lithium, sodium, potassium, rubidium, and cesium, G represents at least one kind of element selected from the group consisting of calcium, strontium, barium, cadmium, titanium, zirconium, vanadium, niobium, tantalum, chromium, tungsten, germanium, tin, yttrium, aluminum, gallium, ruthenium, rhodium, palladium, rhenium, osmium, iridium, platinum, silver, boron, phosphorus, antimony, and tellurium, and a, b, c, d, e, f, x, and y represent an atomic ratio, a is 0.1 to 5, b is 0.1 to 10, c is 2 to 12, d is 0.01 to 5, e is 0.01 to 2, f is 0 to 10, y is 20 to 200, and x is the number of oxygen atom required to satisfy the valence of each of the components except silica. However, c, d, e and f represent a sum of an atomic ratio of each element in a case in which A, D, E and G contain two or more kinds of elements.)

Effect of the Invention

According to the method for producing acrylonitrile of the invention, it is possible to stably maintain a high acrylonitrile yield over a long period of time.

MODE(S) FOR CARRYING OUT THE INVENTION

Hereinafter, the invention will be described in detail.

An aspect of the invention is a method for producing acrylonitrile by the vapor phase catalytic ammoxidation of propylene by molecular oxygen and ammonia in a fluidized bed reactor using a fluidized bed catalyst containing molybdenum and bismuth. The method is characterized in that the vapor phase catalytic ammoxidation reaction is performed while maintaining the adsorbed amount of ammonia per specific surface area ($m^2/g$) of the fluidized bed catalyst during the vapor phase catalytic ammoxidation reaction in the range of 0.05 to 0.6 $\mu mol/m^2$.

In addition, another aspect of the invention is a method for producing acrylonitrile which includes a vapor phase catalytic ammoxidation process of performing the vapor phase catalytic ammoxidation by bringing a source gas containing propylene, molecular oxygen, and ammonia into contact with a fluidized bed catalyst to obtain acrylonitrile. The method is characterized in that the fluidized bed catalyst is a catalyst containing molybdenum and bismuth, and the vapor phase catalytic ammoxidation process is performed while maintaining an adsorbed amount of ammonia per specific surface area ($m^2/g$) of the fluidized bed catalyst in the range of 0.05 to 0.6 $\mu mol/m^2$.

In the method for producing acrylonitrile by the vapor phase catalytic ammoxidation reaction of propylene using a fluidized bed catalyst containing molybdenum and bismuth in a fluidized bed reactor, there is a case in which the acrylonitrile yield time dependently decreases. As a result of intensive investigations on the reason for this, the present inventors have found out that the time-dependent decrease in the acrylonitrile yield is caused by the time dependent change of the ability of the fluidized bed catalyst above to adsorb ammonia. From the result, it has been found out that the time-dependent decrease in the acrylonitrile yield can be suppressed by maintaining the adsorbed amount of ammonia per specific surface area ($m^2/g$) of the fluidized bed catalyst during the vapor phase catalytic ammoxidation reaction in the range of 0.05 to 0.6 $\mu mol/m^2$, thereby the invention has been completed.

In other words, in the invention, it is possible to stably maintain a high acrylonitrile yield over a long period of time by performing the vapor phase catalytic ammoxidation reaction while maintaining the adsorbed amount of ammonia per specific surface area ($m^2/g$) of the fluidized bed catalyst during the vapor phase catalytic ammoxidation reaction process in the range of 0.05 to 0.6 $\mu mol/m^2$. In addition, according to the invention, it is possible to stably maintain a high acrylonitrile yield over a long period of time by maintaining the adsorbed amount of ammonia per specific surface area ($m^2/g$) of the fluidized bed catalyst during the vapor phase catalytic ammoxidation reaction process in the range of 0.05 to 0.6 $\mu mol/m^2$ and thus it is not necessary to add an additive such as molybdenum in excess. Consequently, it is possible to suppress that molybdenum or the like which is volatilized from the additive added in excess is attached to the apparatus for producing acrylonitrile and thus a stable operation over a long period of time is possible.

The lower limit value of the adsorbed amount of ammonia per specific surface area ($m^2/g$) of the fluidized bed catalyst during the vapor phase catalytic ammoxidation reaction process is preferably 0.08 $\mu mol/m^2$ and the upper limit value thereof is preferably 0.5 $\mu mol/m^2$.

In the invention, the adsorbed amount of ammonia per specific surface area ($m^2/g$) of the unreacted fluidized bed catalyst (that is, before the fluidized bed catalyst is utilized in the vapor phase catalytic ammoxidation reaction) is not particularly limited as long as the adsorbed amount of ammonia per specific surface area ($m^2/g$) of the fluidized bed catalyst during the vapor phase catalytic ammoxidation reaction process is maintained in the range of 0.05 to 0.6 $\mu mol/m^2$. The adsorbed amount of ammonia per specific surface area ($m^2/g$) of the unreacted fluidized bed catalyst is preferably 0.08 to 0.5 $\mu mol/m^2$. It is possible to maintain the favorable catalytic performance, that is, a high acrylonitrile yield when the amount of ammonia adsorbed on the fluidized bed catalyst satisfies the condition described above.

Meanwhile, the adsorbed amount of ammonia per specific surface area ($m^2/g$) of the fluidized bed catalyst in the vapor phase catalytic ammoxidation reaction process is a value determined by taking out a part of the fluidized bed catalyst above from the fluidized bed reactor during the process above and quantifying the catalyst by the following method.

The amount of ammonia adsorbed on the fluidized bed catalyst is a value measured in the following manner by referring to the ammonia temperature-programmed desorption method described in Zeolite (Vol. 21, No. 2, p. 45-52, 2004) and Surface Science (Vol. 24, No. 10, p. 635-641, 2003). Meanwhile, it is possible to use an inert gas such as helium, nitrogen, and argon as a carrier gas. A case in which helium is used as a carrier gas will be described below.

The ammonia adsorption amount of the invention refers to a value obtained by measuring the amount of ammonia desorbed from the fluidized bed catalyst by an ammonia adsorption amount measuring apparatus. The specific measurement method will be described below. First, about 0.3 g of the fluidized bed catalyst is charged into the apparatus and then held at 400° C. for one hour while circulating helium at a flow rate of 50 mL/min, thereby the pretreatment of the catalyst is performed.

After the pretreatment is completed, the temperature of the catalyst is lowered to 100° C. and held for 10 minutes in that state.

Subsequently, a mixed gas of 0.1% by volume ammonia and 99.9% by volume helium is circulated for 5 minutes so as to adsorb ammonia on the catalyst.

Thereafter, helium is circulated at a flow rate of 50 mL/min and held for 60 minutes in that state.

Subsequently, the temperature thereof is raised to 500° C. at a raising rate of 10° C./min while circulating helium through the catalyst at a flow rate of 50 mL/min and the ammonia gas desorbed from the catalyst is analyzed by a quadrupole mass spectrometer during the operation so as to quantify the amount of the ammonia desorbed from the catalyst. For the quantification of the amount of ammonia, a calibration curve created separately by introducing a known quantity of ammonia gas into the quadrupole mass spectrometer is used.

The specific surface area ($m^2/g$) of the fluidized bed catalyst is calculated using a specific surface area measuring apparatus (BET method). Meanwhile, the specific surface area can be measured by referring to the conditions described in Annex A (Informative) the use conditions of reference powder for specific surface area of reference powder for specific surface area of Japan Powder Industry Technology Association Standard with regard to the method.

The amount of ammonia quantified by the measurement method described above is taken as the amount of ammonia adsorbed on the fluidized bed catalyst (ammonia adsorption amount), and the result obtained by converting this amount into the amount per specific surface area ($m^2/g$) of the fluidized bed catalyst is taken as the amount of ammonia adsorbed on the fluidized bed catalyst during the vapor phase catalytic ammoxidation reaction.

The amount of by-products such as acrolein or acrylic acid produced increases and thus the acrylonitrile yield decreases in a case in which the adsorbed amount of ammonia per specific surface area ($m^2/g$) of the fluidized bed catalyst during the vapor phase catalytic ammoxidation process is less than the lower limit value, that is, 0.05 Acrolein, acrylic acid, or the like is easily polymerized in the purification process performed at the latter part of the reactor and becomes a cause of the blockage of the line, tower, or the like as a result, and thus a stable operation over a long period of time is difficult in some cases.

On the other hand, the amount of by-products such as carbon dioxide produced increases and thus the acrylonitrile yield decreases in a case in which the adsorbed amount of ammonia per specific surface area ($m^2/g$) of the fluidized bed catalyst during the vapor phase catalytic ammoxidation process is greater than the upper limit value, that is, 0.6 $\mu mol/m^2$. In addition, problems of an increase in the ammonia combustion rate and the deterioration in the ammonia unit requirement also occur. Here, the term "ammonia unit requirement" means the amount of ammonia required to obtain a certain amount of acrylonitrile.

Meanwhile, the reaction may be continued as it is when the ammonia adsorption amount is within the above range, that is, the range from 0.05 to 0.6 $\mu mol/m^2$, but the ammonia adsorption amount may be increased or decreased to the extent in which the ammonia adsorption amount is not out of the range described above.

An aspect of the method for producing acrylonitrile of the invention is characterized in that the vapor phase catalytic ammoxidation process is performed while maintaining the adsorbed amount of ammonia per specific surface area ($m^2/g$) of the fluidized bed catalyst in the range of 0.05 to 0.6 $\mu mol/m^2$. In other words, in the method for producing acrylonitrile of the invention, the vapor phase catalytic ammoxidation reaction process preferably further includes the step of maintaining the adsorbed amount of ammonia per specific surface area in the range of 0.05 to 0.6 $\mu mol/m^2$. It is preferable to use a method for increasing the ammonia adsorption amount or a method for decreasing the ammonia adsorption amount in order to maintain the ammonia adsorption amount in a specific range.

As the method for increasing the amount of ammonia adsorbed on the fluidized bed catalyst during the vapor phase catalytic ammoxidation process, a method of adding a compound having the effect of promoting the adsorption of ammonia may be exemplified. As the compound having the effect of promoting the adsorption of ammonia, a compound containing an element which exhibits acidity such as molybdenum or tungsten may be specifically exemplified. In particular, a method of adding a molybdenum compound such as ammonium molybdate into the reactor is effective as a method for increasing the ammonia adsorption amount.

In addition, a method of adding a catalyst having a large amount of ammonia adsorbed, a method of replacing a part of the catalyst in the reactor with a fresh catalyst, or the like is also effective.

The catalyst having a large amount of ammonia adsorbed can be produced by adjusting the composition of the catalyst, for example, increasing the content of the element having the effect of promoting the adsorption of ammonia such as molybdenum or tungsten. In addition, it is also possible to produce a catalyst having a large amount of ammonia adsorbed by impregnating the fluidized bed catalyst of the invention with an element having the effect of promoting the adsorption of ammonia. Examples of the "element having the effect of promoting the adsorption of ammonia" may include molybdenum and tungsten.

On the other hand, as the method to decrease the amount of ammonia adsorbed on the fluidized bed catalyst during the vapor phase catalytic ammoxidation process, a method of adding a compound having the effect of inhibiting the adsorption of ammonia may be exemplified. As the compound having the effect of inhibiting the adsorption of ammonia, specifically a compound containing an element which exhibits basicity such as potassium, rubidium, or cesium may be exemplified. In addition, a method of adding a catalyst having a small amount of ammonia adsorbed, a method of replacing a part of the catalyst in the reactor with a catalyst having a decreased ammonia adsorption amount resulted from use in the reaction, or the like is also effective.

The catalyst having a small amount of ammonia adsorbed can be produced by adjusting the composition of the catalyst, for example, increasing the content of the element having the effect of inhibiting the adsorption of ammonia such as potassium, rubidium, or cesium. In addition, it is also possible to produce a catalyst having a small amount of ammonia adsorbed by impregnating the fluidized bed catalyst of the invention with an element having the effect of inhibiting the adsorption of ammonia. Examples of the "element having the effect of inhibiting the adsorption of ammonia" may include potassium, rubidium, and cesium.

In addition, molybdenum or the like which is an element promoting the adsorption of ammonia has a property to easily volatile during the vapor phase catalytic ammoxidation process compared with other components constituting the catalyst. By utilizing this property, the amount of ammonia adsorbed on the fluidized bed catalyst during the reaction may be controlled such that the volatilization of molybdenum or the like is promoted (or reduced) by temporarily raising (or lowering) the reaction temperature.

The timing for adding the compound having the effect of promoting the adsorption of ammonia or the compound having the effect of inhibiting the adsorption of ammonia or the addition amount thereof is not particularly limited as long as the effect of the invention is exhibited by the addition timing or the addition amount, but the amount of ammonia adsorbed on the fluidized bed catalyst during the reaction tends to decrease as the vapor phase catalytic ammoxidation reaction proceeds. Consequently, the addition timing or the addition amount is preferably set such that the adsorbed amount of ammonia per specific surface area (m²/g) of the fluidized bed catalyst during the vapor phase catalytic ammoxidation reaction is in the range described above.

Meanwhile, the method for controlling the amount of ammonia adsorbed on the fluidized bed catalyst in the reactor is not limited to the methods described above, but the control of the amount of ammonia adsorbed on the fluidized bed catalyst can be carried out by an arbitrary known method.

In the method for producing acrylonitrile of the invention, the vapor phase catalytic ammoxidation process is performed using a catalytic layer prepared by filling a fluidized bed catalyst in a fluidized bed reactor and by passing a source gas containing propylene, molecular oxygen, and ammonia through the catalytic layer.

The source gas is not particularly limited as long as the effect of the invention is exhibited by the source gas, but the source gas preferably has a ratio of propylene/ammonia/oxygen in the range of 1/1.0 to 2.0/1.0 to 5.0 (molar ratio).

The supply source of molecular oxygen which is an oxygen source is not particularly limited as long as the effect of the invention is exhibited by as the supply source of molecular oxygen, but air is preferably used.

The source gas may be diluted with an inert gas such as nitrogen or carbon dioxide or saturated hydrocarbon or may also be used by mixing with pure oxygen to increase the oxygen concentration.

The reaction temperature of the vapor phase ammoxidation reaction is preferably 350 to 500° C. and the reaction pressure thereof is preferably within the range of the normal pressure (100 kPa) to 500 kPa. The contact time of the fluidized bed catalyst with the reaction gas is preferably 0.1 to 20 seconds.

The fluidized bed catalyst used in the invention is not particularly limited as long as a fluidized bed catalyst satisfies the requirements described above, contains molybdenum and bismuth, and exhibits the effect of the invention, but it is preferable to have a composition represented by the following Formula (1) in terms of obtaining a high acrylonitrile yield.

$$Mo_{12}Bi_aFe_bA_cD_dE_eG_fO_x \cdot (SiO_2)_y \quad (1)$$

In Formula (1), Mo, Bi, Fe, O, and $SiO_2$ represent molybdenum, bismuth, iron, oxygen, and silica, respectively, A represents at least one kind of element selected from the group consisting of nickel, cobalt, zinc, magnesium, manganese, and copper, D represents at least one kind of element selected from the group consisting of lanthanum, cerium, praseodymium, neodymium, and samarium, E represents at least one kind of element selected from the group consisting of lithium, sodium, potassium, rubidium, and cesium, G represents at least one kind of element selected from the group consisting of calcium, strontium, barium, cadmium, titanium, zirconium, vanadium, niobium, tantalum, chromium, tungsten, germanium, tin, yttrium, aluminum, gallium, ruthenium, rhodium, palladium, rhenium, osmium, iridium, platinum, silver, boron, phosphorus, antimony, and tellurium, and a, b, c, d, e, f, x, and y represent an atomic ratio, a is 0.1 to 5, b is 0.1 to 10, c is 2 to 12, d is 0.01 to 5, e is 0.01 to 2, f is 0 to 10, y is 20 to 200, and x is the number of oxygen atom required to satisfy the valence of each of the components except silica. However, c, d, e and f represent a sum of an atomic ratio of each element in a case in which A, D, E and G contain two or more kinds of elements.

The method for producing the fluidized bed catalyst used in the invention is not particularly limited as long as the effect of the present invention is exhibited by a method, and the fluidized bed catalyst may be produced based on the method for producing a catalyst described in, for example, Patent Documents 1 to 18 described above. Specifically, it is possible to exemplify a method in which a solution or aqueous slurry containing the starting material of each of the elements constituting the fluidized bed catalyst is prepared, the solution or aqueous slurry thus obtained is dried, and then the dry product thus obtained is calcined. In other words, the method for producing the fluidized bed catalyst of invention is preferably a method for producing the fluidized bed catalyst which includes step (I) of preparing a solution or aqueous slurry by mixing the respective elements constituting the fluidized bed catalyst and step (II) of drying the solution or aqueous slurry obtained in step (I) above and then calcining the dry product thus obtained.

In step (I), the solution or aqueous slurry may contain all of the desired elements constituting the fluidized bed catalyst at the desired atomic ratio. In addition, a solution or aqueous slurry containing some of the elements constituting the fluidized bed catalyst may be prepared and then the rest of the elements may be added to the catalyst composition dried or f calcined by a method such as impregnation.

The starting material of each of the elements constituting the fluidized bed catalyst are determined according to its purpose, application, or the like, and it is preferable to use an oxide, or a nitrate, a carbonate, an organic acid salt, a hydroxide, an ammonium salt, or the like which is able to be easily formed into an oxide by igniting, or a mixture thereof.

A solution or aqueous slurry is obtained by mixing these starting materials as solids or after preparing solutions thereof by dissolving in water, dilute nitric acid, or the like. In addition, the fluidized bed catalyst of the invention contains silica, and silica sol is preferably used as the silica.

Upon the pH adjustment of the solution or aqueous slurry, the pH adjustment may be performed by the addition of nitric acid, aqueous ammonia, or the like if necessary, or performed by a concentration treatment, or a heat treatment.

Step (II) is a step of drying the solution or aqueous slurry obtained in step (I) above and then calcining the dry product thus obtained. In step (II), it is preferable to obtain a spherical dry product (dry particles) as possible by drying the solution or slurry containing the elements constituting the fluidized bed catalyst. Usually, drying is performed by spray drying. It is possible to use a common dryer such as a rotary disk type or a nozzle type as a dryer. The conditions for drying can be appropriately adjusted in order to obtain a catalyst having the preferred particle size distribution as a fluidized bed catalyst.

The catalytic activity is exerted by calcining the dry particles thus obtained. The calcination temperature is preferably 300 to 1000° C. The catalytic activity is hardly exerted when the firing temperature is lower than the lower limit value above, that is, 300° C. In contrast, the activity is likely to deteriorate or the acrylonitrile yield is likely to decrease when the calcination temperature is higher than the upper limit value above, that is, 1000° C. In other words, it is preferable that the calcination temperature be 300 to 1000° C. since the catalytic activity is easily exerted and the acrylonitrile yield hardly decreases.

The calcination time is preferably 0.5 hour or longer since the catalytic activity is difficult to be sufficiently exerted when the calcination time is too short. The upper limit thereof is not particularly limited but is usually 20 hours or shorter since the performance of the catalyst is not enhanced to more than a certain extent even though the calcination time is extended longer than the required time. In other words, the calcination time is preferably 0.5 to 20 hours.

The furnace used for calcination is not particularly limited, and it is possible to use a box furnace, a rotary kiln, a fluidized bed furnace, or the like. For the production of fluidized bed catalyst, it is preferable to use a rotary kiln or a fluidized bed furnace by which calcination is performed while fluidizing the particles, and a fluidized bed furnace is particularly preferable in terms that uniform calcination is possible. It is preferable to perform calcination by dividing into two or more times since the acrylonitrile yield or the physical properties of the catalyst such as particle strength is improved.

In order to set the composition of the catalyst within the range of Formula (1) above, it is possible to appropriately select, for example, the amount of each of the catalyst starting materials added in step (I) of preparing a solution or aqueous slurry described above or the amount of the catalyst starting materials added at each step until the drying step after the step of preparing a solution or aqueous slurry. In addition, in step (II), the amount of the catalyst starting materials added by impregnation or the like may be appropriately selected in the case of producing the catalyst by a method of impregnating the catalyst after drying or the like.

The composition of the catalyst can be confirmed by performing the elemental analysis by ICP (inductively coupled plasma) high-frequency atomic emission spectroscopy, XRF (X-ray fluorescence) analysis, atomic absorption spectrophotometry, or the like. It is also possible to calculate the composition of the catalyst from the charged amount of each of the starting materials used at the time of producing the catalyst in the case of not using a significantly highly volatile element.

According to the method for producing acrylonitrile of the invention described above, it is possible to suppress a time-dependent decrease in the acrylonitrile yield and to stably maintain a high acrylonitrile yield over a long period of time by performing the vapor phase catalytic ammoxidation reaction while maintaining the adsorbed amount of ammonia per specific surface area (m$^2$/g) of the fluidized bed catalyst during the reaction in the range of 0.05 to 0.6 µmol/m$^2$ during the vapor phase catalytic ammoxidation reaction. Consequently, the method for producing acrylonitrile of the invention is an economically advantageous method.

EXAMPLES

Hereinafter, the embodiments and effects of the invention will be specifically described with reference to Examples, but the invention is not limited to the present Examples.

The method for producing the fluidized bed catalyst used in each Example is described below. Meanwhile, the composition of the fluidized bed catalyst was determined from the charged amount of each of the starting materials used in the production of the catalyst.

In addition, the method for the activity test of the fluidized bed catalyst and the method for measuring the amount of ammonia adsorbed on the fluidized bed catalyst are described below.

[Production of Fluidized Bed Catalyst]

<Fluidized Bed Catalyst 1>

First, to 8724.4 g of 20% by mass silica sol, a solution prepared by dissolving 1025.5 g of ammonium paramolybdate in 2500 g of water was added under stirring and heated to 40° C. (liquid A).

Separately, 164.4 g of bismuth nitrate was dissolved in 1000 g of 17% by mass nitric acid under stirring, and 254.2 g of iron nitrate (III), 774.1 g of nickel nitrate, 144.0 g of zinc nitrate, 69.5 g of manganese nitrate, 41.9 g of lanthanum nitrate, 4.2 g of praseodymium nitrate, 19.6 g of potassium nitrate, and 9.4 g of cesium nitrate were added to this liquid in order and heated to 45° C. so as to obtain a slurry material (liquid B).

Liquid B was added to liquid A under stirring so as to obtain an aqueous slurry.

The aqueous slurry thus obtained was dried by a rotary disk type spray dryer while controlling the temperature of hot air at 280° C. at the dryer inlet and 150° C. at the dryer outlet.

The dry product thus obtained was calcined at 300° C. for 2 hours and subsequently at 450° C. for 2 hours, and then calcined at 600° C. for 3 hours by a fluidized bed furnace so as to obtain fluidized bed catalyst 1.

The composition of fluidized bed catalyst 1 thus obtained was as follows.

$$Mo_{12}Bi_{0.7}Fe_{1.3}Ni_{5.5}Zn_1Mn_{0.5}La_{0.2}Pr_{0.02}K^{0.4}Cs_{0.1}O_x \cdot (SiO_2)_{60}$$

Here, x is the number of oxygen atom required to satisfy the valence of each of the components above except silica. It should be noted that the composition of fluidized bed catalyst 1 is presented in Table 1 as well but the description of oxygen and the number (x) of oxygen atom is not presented in Table 1.

<Fluidized Bed Catalyst 2>

To 450 g of pure water heated at 50° C., 222.2 g of ammonium paramolybdate was added and dissolved, and then the liquid amount was adjusted to 530 mL by adding pure water thereto so as to prepare liquid C.

To 3000 g of fluidized bed catalyst 1, liquid C was added little by little so as to obtain a mixture impregnated with liquid C.

This mixture was calcined at 450° C. for 3 hours in a rotary calcining furnace so as to obtain fluidized bed catalyst 2.

The composition of fluidized bed catalyst 2 thus obtained was as follows.

$$Mo_{14.6}Bi_{0.7}Fe_{1.3}Ni_{5.5}Zn_1Mn_{0.5}La_{0.2}Pr_{0.02}K_{0.2}K_{0.4}Cs_{0.1}(SiO_2)_{60}$$

Here, x is the number of oxygen atom required to satisfy the valence of each of the components above except silica. It should be noted that the composition of fluidized bed catalyst 2 is presented in Table 1 as well but the description of oxygen and the number (x) of oxygen atom is not presented in Table 1.

<Fluidized Bed Catalyst 3>

To 280 g of pure water heated at 50° C., 4.9 g of potassium nitrate and 28.3 g of cesium nitrate were added and dissolved, and then the liquid amount was adjusted to 520 mL by adding pure water thereto so as to prepare liquid D.

To 3000 g of fluidized bed catalyst 1, liquid D was added little by little so as to obtain a mixture impregnated with liquid D.

This mixture was calcined at 450° C. for 3 hours in a rotary calcining furnace so as to obtain fluidized bed catalyst 3.

The composition of fluidized bed catalyst 3 thus obtained was as follows.

$$Mo_{12}Bi_{0.7}Fe_{1.3}Ni_{5.5}Zn_1Mn_{0.5}La_{0.2}Pr_{0.02}K_{0.5}Cs_{0.4}(SiO_2)_{60}$$

Here, x is the number of oxygen atom required to satisfy the valence of each of the components above except silica. It should be noted that the composition of fluidized bed catalyst 3 is presented in Table 1 as well but the description of oxygen and the number (x) of oxygen atom is not presented in Table 1.

<Fluidized Bed Catalyst 4>

First, to 6325.9 g of 20% by mass silica sol, a solution prepared by dissolving 1274.7 g of ammonium paramolybdate in 2500 g of water was added under stirring and heated to 40° C. (liquid E).

Separately, 145.9 g of bismuth nitrate was dissolved in 1000 g of 17% by mass nitric acid under stirring, and 437.5 g of iron nitrate (III), 349.9 g of nickel nitrate, 700.4 g of cobalt nitrate, 462.8 g of magnesium nitrate, 52.1 g of lanthanum nitrate, 156.8 g of cerium nitrate, 35.5 g of rubidium nitrate, and 8.8 g of antimony trioxide were added to this liquid in order and heated to 45° C. so as to obtain a slurry material (liquid F).

Liquid F was added to liquid E under stirring, and then 139.5 g of a 50% by mass aqueous solution of ammonium metatungstate (50% by mass as WO₃) heated to 45° C. was added thereto so as to obtain an aqueous slurry.

The aqueous slurry thus obtained was dried by a rotary disk type spray dryer while controlling the temperature of hot air at 285° C. at the dryer inlet and 155° C. at the dryer outlet.

The dry product thus obtained was prefired at 300° C. for 2 hours and subsequently at 450° C. for 2 hours, and then calcined at 540° C. for 3 hours by a fluidized bed furnace so as to obtain fluidized bed catalyst 4.

The composition of fluidized bed catalyst 4 thus obtained was as follows.

$$Mo_{12}Bi_{0.5}Fe_{1.8}Ni_2Co_4Mg_3La_{0.2}Ce_{0.6}Rb_{0.4}W_{0.5}Sb_{0.1}O_x(SiO_2)_{35}$$

Here, x is the number of oxygen atom required to satisfy the valence of each of the components above except silica. It should be noted that the composition of fluidized bed catalyst 4 is presented in Table 1 as well but the description of oxygen and the number (x) of oxygen atom is not presented in Table 1.

<Fluidized Bed Catalyst 5>

Fluidized bed catalyst 5 was obtained by the same production method as in fluidized bed catalyst 4 except that the amount of rubidium nitrate used at the time of preparing liquid F was changed from 35.5 g to 0.9 g in the production of fluidized bed catalyst 4.

The composition of fluidized bed catalyst 5 thus obtained was as follows.

$$Mo_{12}Bi_{0.5}Fe_{1.8}Ni_2Co_4Mg_3La_{0.2}Ce_{0.6}Rb_{0.01}W_{0.5}Sb_{0.1}(SiO_2)_{35}$$

Here, x is the number of oxygen atom required to satisfy the valence of each of the components above except silica. It should be noted that the composition of fluidized bed catalyst 5 is presented in Table 1 as well but the description of oxygen and the number (x) of oxygen atom is not presented in Table 1.

<Fluidized Bed Catalyst 6>

Fluidized bed catalyst 6 was obtained by the same production method as in fluidized bed catalyst 4 except that the amount of ammonium paramolybdate used at the time of preparing liquid E was changed from 1274.7 g to 1062.3 g in the production of fluidized bed catalyst 4.

The composition of fluidized bed catalyst 6 thus obtained was as follows.

$$Mo_{10}Bi_{0.5}Fe_{1.8}Ni_2Co_4Mg_3La_{0.2}Ce_{0.6}Rb_{0.4}W_{0.5}Sb_{0.1}(SiO_2)_{35}$$

Here, x is the number of oxygen atom required to satisfy the valence of each of the components above except silica. It should be noted that the composition of fluidized bed catalyst 6 is presented in Table 1 as well but the description of oxygen and the number (x) of oxygen atom is not presented in Table 1.

TABLE 1

Composition of catalyst (atomic ratio)

| | Mo | Bi | Fe | A | | | D | | E | | G | | | SiO₂ |
|---|---|---|---|---|---|---|---|---|---|---|---|---|---|---|
| Fluidized bed catalyst 1 | 12 | 0.7 | 1.3 | Ni 5.5 | Zn 1 | Mn 0.5 | La 0.2 | Pr 0.02 | K 0.4 | Cs 0.1 | | | | 60 |
| Fluidized bed catalyst 2 | 14.6 | 0.7 | 1.3 | Ni 5.5 | Zn 1 | Mn 0.5 | La 0.2 | Pr 0.02 | K 0.4 | Cs 0.1 | | | | 60 |
| Fluidized bed catalyst 3 | 12 | 0.7 | 1.3 | Ni 5.5 | Zn 1 | Mn 0.5 | La 0.2 | Pr 0.02 | K 0.5 | Cs 0.4 | | | | 60 |
| Fluidized bed catalyst 4 | 12 | 0.5 | 1.8 | Ni 2 | Co 4 | Mg 3 | La 0.2 | | Ce 0.6 | | Rb 0.4 | W 0.5 | Sb 0.1 | 35 |
| Fluidized bed catalyst 5 | 12 | 0.5 | 1.8 | Ni 2 | Co 4 | Mg 3 | La 0.2 | | Ce 0.6 | | Rb 0.01 | W 0.5 | Sb 0.1 | 35 |
| Fluidized bed catalyst 6 | 10 | 0.5 | 1.8 | Ni 2 | Co 4 | Mg 3 | La 0.2 | | Ce 0.6 | | Rb 0.4 | W 0.5 | Sb 0.1 | 35 |

Activity Test of Fluidized Bed Catalyst

The acrylonitrile synthesis reaction by vapor phase catalytic ammoxidation reaction of propylene was performed using the fluidized bed catalyst thus obtained in the following manner.

A fluidized bed reactor having a catalyst flow section with an inner diameter of 55 mm and a height of 2000 mm was filled with the fluidized bed catalyst so as to have a contact time of 2.8 seconds. The contact time of the fluidized bed catalyst with the reaction gas was determined by the following Equation.

Contact time(s)=catalyst volume by apparent bulk density standard (mL)/amount of supplied source gas in terms of reaction condition (mL/sec)

Air was used as the oxygen source, and the source gas having a composition of propylene:ammonia:oxygen:water vapor=1:1.2:2.0:0.5 (molar ratio) was fed into the catalytic layer at a gas linear velocity of 17 cm/sec. The reaction pressure was 200 kPa and the reaction temperature was 435° C.

A gas chromatography was used to quantify the reaction product, and the analysis was performed one or more times for every 100 hours. At that time, the amount of the catalyst was appropriately adjusted such that the conversion ratio of propylene was 97.8 to 98.2%. Specifically, the amount of the catalyst was adjusted by adding the fresh catalyst in a case in which the conversion ratio of propylene was less than this range. In addition, the conversion ratio of propylene was adjusted by taking out the catalyst from the reactor in a case in which the conversion ratio of propylene was greater than this range.

The conversion ratio of propylene, the acrylonitrile yield, and the ammonia combustion rate were determined by the following Equations.

Conversion ratio of propylene (%)={(carbon mass of supplied propylene−carbon mass of unreacted propylene)/(carbon mass of supplied propylene)}×100

Acrylonitrile yield (%)={(carbon mass of produced acrylonitrile)/(carbon mass of supplied propylene)}×100

Ammonia combustion rate (%)={(nitrogen mass of supplied ammonia−nitrogen mass of unreacted ammonia−nitrogen mass of trapped nitrogen-containing organic compounds)/(nitrogen mass of supplied ammonia)}×100

Measurement of Ammonia Adsorption Amount

The amount of ammonia adsorbed on the fluidized bed catalyst was measured in the following manner by referring to the ammonia temperature-programmed desorption method described in Zeolite (Vol. 21, No. 2, p. 45-52, 2004) and Surface Science (Vol. 24, No. 10, p. 635-641, 2003). Meanwhile, a full automatic temperature-programmed desorption gas analyzer ("multitasking TPD" manufactured by BEL Japan, Inc.) was used as the ammonia adsorption amount measuring apparatus. In addition, helium was used as the carrier gas.

First, about 0.3 g of the fluidized bed catalyst to be the target was taken and set in a cell for measurement of the full automatic temperature-programmed desorption gas analyzer. The temperature of the catalyst was set to 400° C. and held for one hour while circulating helium through this catalyst at a flow rate of 50 mL/min, thereby the pretreatment of the catalyst was performed.

After the pretreatment was completed, the temperature of the catalyst was lowered to 100° C. and held for 10 minutes in that state.

Subsequently, a mixed gas of 0.1% by volume ammonia and 99.9% by volume helium was circulated for 5 minutes so as to adsorb ammonia on the catalyst.

Thereafter, helium was circulated at a flow rate of 50 mL/min and held for 60 minutes in that state.

Subsequently, the temperature thereof was raised to 500° C. at a raising rate of 10° C./min while circulating helium through the catalyst at a flow rate of 50 mL/min and the ammonia gas desorbed from the catalyst was analyzed by a quadrupole mass spectrometer during the operation so as to quantify the amount of the ammonia gas desorbed from the catalyst. For the quantification of the amount of ammonia, a calibration curve created separately by introducing ammonia gas with a known quantity into the quadrupole mass spectrometer was used.

The amount of ammonia quantified by the measurement method described above was taken as the amount of ammonia adsorbed on the catalyst (ammonia adsorption amount), and the result obtained by converting this amount into the amount per specific surface area ($m^2/g$) of the catalyst was taken as the amount of ammonia adsorbed on the fluidized bed catalyst during the vapor phase catalytic ammoxidation reaction.

Meanwhile, the setting conditions of the quadrupole mass spectrometer are as follows.

<Setting Conditions>
Cumulative number: 5 times
MCP (Micro Channel Plate, photomultiplier device voltage): 720 eV·Emission (emission current): 2 mA
IE (Ion Energy, ionization energy): 8 V
EE (Electron Energy, electron energy): 70 eV
Scan Time (scan time): 300 ms The amount of ammonia adsorbed ($\mu mol/g$) per 1 g of the catalyst was determined from the amount of ammonia quantified by the measurement method described above and the weight of the catalyst used in the measurement.

Measurement of Specific Surface Area

The specific surface area ($m^2/g$) of the fluidized bed catalyst was calculated using a specific surface area measuring apparatus (BET method). Meanwhile, the specific surface area was measured in the following manner by referring to the conditions described in Annex A (Informative) the use conditions of reference powder for specific surface area of reference powder for specific surface area assay powder of Japan Powder Industry Technology Association Standard with regard to the method. Meanwhile, a BET specific surface area measuring apparatus "Macsorb HM Model-1208" manufactured by Mountech Co., Ltd.) was used as the specific surface area measuring apparatus.

First, about 0.5 g of the fluidized bed catalyst to be the target was taken and set in a cell for measurement of the BET specific surface area measuring apparatus. The temperature of the catalyst was set to 200° C. and held for 40 minutes while circulating a nitrogen gas through this catalyst, thereby the pretreatment of the catalyst was performed.

After the pretreatment was completed, the resultant was left to cool at room temperature for 4 minutes. Subsequently, the resultant was cooled to the temperature of liquid nitrogen while circulating a mixed gas of 30% by volume nitrogen and 70% by volume helium at a flow rate of 25 ml/min so as to adsorb nitrogen on the catalyst. Nitrogen was sufficiently adsorbed on the catalyst until the amount of nitrogen in the outlet gas is stabilized at a constant amount through the detection thereof by a TCD detector.

Thereafter, the sufficiently adsorbed nitrogen was desorbed at room temperature and the desorbed amount thereof was detected by the same TCD detector.

After the desorption was completed, the nitrogen gas filled in the column in the apparatus was pushed out to the mixed gas line to perform the calibration. The weight of the sample cell at a room temperature after the completion of the measurement was measured, and the weight of the catalyst was calculated. The specific surface area ($m^2/g$) per 1 g of the catalyst was calculated from the nitrogen desorption amount, the value of calibration, and the weight of the sample.

The amount of ammonia adsorbed ($\mu mol/m^2$) per specific surface area of the catalyst was calculated by the following Equation using the values of the ammonia adsorption amount (μmol/g) and specific surface area (m²/g) of the catalyst which are determined by the measurement methods described above, respectively.

Adsorbed amount of ammonia per specific surface area (m²/g) of fluidized bed catalyst (μmol/m²)=ammonia adsorption amount (μmol/g)/specific surface area of fluidized bed catalyst (m²/g)

Example 1

The activity test and the measurement of the ammonia adsorption amount and specific surface area of the catalyst taken out from the reactor were performed in the following manner.

The acrylonitrile synthesis reaction by the vapor phase catalytic ammoxidation reaction was performed using fluidized bed catalyst 1. Meanwhile, the adsorbed amount of ammonia per specific surface area of the unreacted fluidized bed catalyst was 0.42 μmol/m².

The analysis of the reaction gas was performed in 100 hours from the start of the reaction and thus the conversion ratio of propylene, the acrylonitrile yield, and the ammonia combustion rate were determined. In addition, about 5 g of the catalyst was taken out from the reactor immediately after the analysis of the reaction gas and then subjected to the measurement of the ammonia adsorption amount and specific surface area thereof in 100 hours from the start of the reaction.

Subsequently, the reaction was continued, and the analysis of the reaction gas was performed in 300 hours from the start of the reaction and thus the conversion ratio of propylene, the acrylonitrile yield, and the ammonia combustion rate were determined. In addition, about 5 g of the catalyst was taken out from the reactor immediately after the analysis of the reaction gas and then subjected to the measurement of the ammonia adsorption amount and specific surface area thereof in 300 hours from the start of the reaction. In 325 hours from the start of the reaction, ammonium molybdate was added into the reactor in an amount corresponding to 3% of the mass of the catalyst in the reactor and then the reaction was continued.

The analysis of the reaction gas was performed in 500 hours from the start of the reaction and thus the conversion ratio of propylene, the acrylonitrile yield, and the ammonia combustion rate were determined. In addition, about 5 g of the catalyst was taken out from the reactor immediately after the analysis of the reaction gas and then subjected to the measurement of the ammonia adsorption amount and specific surface area thereof in 500 hours from the start of the reaction. In 525 hours from the start of the reaction, the catalyst was taken out from the reactor in an amount corresponding to 7% of the mass of the catalyst in the reactor and fluidized bed catalyst 2 was added into the reactor in an amount equal to that of the catalyst taken out, and then the reaction was continued.

The analysis of the reaction gas was performed in 700 hours from the start of the reaction and thus the conversion ratio of propylene, the acrylonitrile yield, and the ammonia combustion rate were determined. In addition, about 5 g of the catalyst was taken out from the reactor immediately after the analysis of the reaction gas and then subjected to the measurement of the ammonia adsorption amount and specific surface area thereof in 700 hours from the start of the reaction. In 725 hours from the start of the reaction, fluidized bed catalyst 3 was added into the reactor in an amount corresponding to 4% of the mass of the catalyst in the reactor and then the reaction was continued.

The analysis of the reaction gas was performed in 1000 hours from the start of the reaction and thus the conversion ratio of propylene, the acrylonitrile yield, and the ammonia combustion rate were determined. In addition, about 5 g of the catalyst was taken out from the reactor immediately after the analysis of the reaction gas and then subjected to the measurement of the ammonia adsorption amount and specific surface area thereof in 1000 hours from the start of the reaction. The results of these are presented in Table 2.

Example 2

The acrylonitrile synthesis reaction by the vapor phase catalytic ammoxidation reaction was performed using the same fluidized bed catalyst 1 as in Example 1 in the following manner.

The operation was performed in the same manner as in Example 1 until 525 hours from the start of the reaction, and the catalyst was taken out from the reactor in an amount corresponding to 15% of the mass of the catalyst in the reactor and fluidized bed catalyst 2 was added into the reactor in an amount equal to that of the catalyst taken out in 525 hours from the start of the reaction, and then the reaction was continued. In addition, the operation was performed in the same manner as in Example 1 after this as well.

The analysis of the reaction gas was performed in 100, 300, 500, 700, and 1000 hours from the start of the reaction and thus the conversion ratio of propylene, the acrylonitrile yield, and the ammonia combustion rate were determined. In addition, about 5 g of the catalyst was taken out from the reactor immediately after each of the analyses of the reaction gas and then subjected to the measurement of the ammonia adsorption amount and specific surface area thereof in 100, 300, 500, 700, and 1000 hours from the start of the reaction.

The results of these are presented in Table 2.

Example 3

The acrylonitrile synthesis reaction by the vapor phase catalytic ammoxidation reaction was performed using fluidized bed catalyst 4. Meanwhile, the adsorbed amount of ammonia per specific surface area of the unreacted fluidized bed catalyst was 0.18 μmol/m².

The analysis of the reaction gas was performed in 100 hours from the start of the reaction and thus the conversion ratio of propylene, the acrylonitrile yield, and the ammonia combustion rate were determined. In addition, about 5 g of the catalyst was taken out from the reactor immediately after the analysis of the reaction gas and then subjected to the measurement of the ammonia adsorption amount and specific surface area thereof in 100 hours from the start of the reaction.

Subsequently, the reaction was continued, and the analysis of the reaction gas was performed in 300 hours from the start of the reaction and thus the conversion ratio of propylene, the acrylonitrile yield, and the ammonia combustion rate were determined. In addition, about 5 g of the catalyst was taken out from the reactor immediately after the analysis of the reaction gas and then subjected to the measurement of the ammonia adsorption amount and specific surface area thereof in 300 hours from the start of the reaction. In 325 hours from the start of the reaction, fluidized bed catalyst 5 was added into the reactor in an amount corresponding to 2% of the mass of the catalyst in the reactor, and then the reaction was continued.

The analysis of the reaction gas was performed in 500 hours from the start of the reaction and thus the conversion ratio of propylene, the acrylonitrile yield, and the ammonia combustion rate were determined. In addition, about 5 g of the catalyst was taken out from the reactor immediately after the analysis of the reaction gas and then subjected to the measurement of the ammonia adsorption amount and specific surface area thereof in 500 hours from the start of the reaction. In 525 hours from the start of the reaction, molybdenum trioxide was added into the reactor in an amount corresponding to 6% of the mass of the catalyst in the reactor and then the reaction was continued.

The analysis of the reaction gas was performed in 700 hours from the start of the reaction and thus the conversion ratio of propylene, the acrylonitrile yield, and the ammonia combustion rate were determined. In addition, about 5 g of the catalyst was taken out from the reactor immediately after the analysis of the reaction gas and then subjected to the measurement of the ammonia adsorption amount and specific surface area thereof in 700 hours from the start of the reaction. In 725 hours from the start of the reaction, fluidized bed catalyst 6 was added into the reactor in an amount corresponding to 2% of the mass of the catalyst in the reactor and then the reaction was continued.

The analysis of the reaction gas was performed in 1000 hours from the start of the reaction and thus the conversion ratio of propylene, the acrylonitrile yield, and the ammonia combustion rate were determined. In addition, about 5 g of the catalyst was taken out from the reactor immediately after the analysis of the reaction gas and then subjected to the measurement of the ammonia adsorption amount and specific surface area thereof in 1000 hours from the start of the reaction.

The results of these are presented in Table 2.

Comparative Example 1

The same operation as in Example 3 was performed using the same fluidized bed catalyst 4 as in Example 3 except that fluidized bed catalysts 5 and 6 and molybdenum trioxide were not added during the reaction.

The analysis of the reaction gas was performed in 100, 300, 500, 700, and 1000 hours from the start of the reaction and thus the conversion ratio of propylene, the acrylonitrile yield, and the ammonia combustion rate were determined. In addition, about 5 g of the catalyst was taken out from the reactor immediately after each of the analyses of the reaction gas and then subjected to the measurement of the ammonia adsorption amount and specific surface area thereof in 100, 300, 500, 700, and 1000 hours from the start of the reaction.

The results of these are presented in Table 2.

Comparative Example 2

The acrylonitrile synthesis reaction by the vapor phase catalytic ammoxidation reaction was performed using the same fluidized bed catalyst 1 as in Example 1 in the following manner.

The analysis of the reaction gas was performed in 100 hours from the start of the reaction and thus the conversion ratio of propylene, the acrylonitrile yield, and the ammonia combustion rate were determined. In addition, about 5 g of the catalyst was taken out from the reactor immediately after the analysis of the reaction gas and then subjected to the measurement of the ammonia adsorption amount and specific surface area thereof in 100 hours from the start of the reaction. In 125 hours from the start of the reaction, the catalyst was taken out from the reactor in an amount corresponding to 15% of the mass of the catalyst in the reactor and fluidized bed catalyst 2 was added into the reactor in an amount equal to that of the catalyst taken out, and then the reaction was continued.

The analysis of the reaction gas was performed in 300 hours from the start of the reaction. In addition, about 5 g of the catalyst was taken out from the reactor immediately after the analysis of the reaction gas and then subjected to the measurement of the ammonia adsorption amount and specific surface area thereof in 300 hours from the start of the reaction.

The results of these are presented in Table 2.

TABLE 2

| | Catalyst | Elapsed time [hour] | Specific surface area of catalyst [$m^2/g$] | Adsorbed amount of ammonia per specific surface area of catalyst [$\mu mol/m^2$] | Activity test Conversion ratio of propylene [%] | Acrylonitrile yield [%] | Ammonia combustion rate [%] |
|---|---|---|---|---|---|---|---|
| Example 1 | Fluidized bed catalyst 1 | 0 | 45 | 0.42 | — | — | — |
| | | 100 | 43 | 0.37 | 98.5 | 82.1 | 11.8 |
| | | 300 | 41 | 0.29 | 98.2 | 82.6 | 9.9 |
| | | 500 | 40 | 0.25 | 98.0 | 82.5 | 8.9 |
| | | 700 | 40 | 0.47 | 97.8 | 81.9 | 13.7 |
| | | 1000 | 39 | 0.09 | 98.2 | 82.0 | 3.9 |
| Example 2 | Fluidized bed catalyst 1 | 0 | 45 | 0.42 | — | — | — |
| | | 100 | 43 | 0.37 | 98.5 | 82.1 | 12.0 |
| | | 300 | 41 | 0.29 | 98.2 | 82.6 | 10.0 |
| | | 500 | 40 | 0.25 | 98.0 | 82.5 | 8.8 |
| | | 700 | 41 | 0.57 | 97.8 | 81.1 | 18.0 |
| | | 1000 | 40 | 0.2 | 98.2 | 82.4 | 7.9 |
| Example 3 | Fluidized bed catalyst 4 | 0 | 34 | 0.18 | — | — | — |
| | | 100 | 33 | 0.11 | 98.1 | 82.0 | 4.2 |
| | | 300 | 32 | 0.07 | 97.7 | 81.0 | 2.8 |
| | | 500 | 31 | 0.35 | 98.1 | 82.2 | 10.5 |
| | | 700 | 31 | 0.33 | 97.9 | 82.3 | 9.9 |
| | | 1000 | 29 | 0.19 | 98.2 | 82.4 | 6.4 |
| Comparative Example 1 | Fluidized bed catalyst 4 | 0 | 34 | 0.18 | — | — | — |
| | | 100 | 33 | 0.11 | 98.0 | 81.9 | 4.2 |
| | | 300 | 32 | 0.07 | 97.8 | 81.1 | 2.9 |
| | | 500 | 30 | 0.05 | 98.1 | 78.7 | 1.4 |
| | | 700 | 28 | 0.04 | 98.1 | 78.1 | 0.9 |
| | | 1000 | 26 | 0.03 | 97.9 | 77.8 | 0.7 |

TABLE 2-continued

| Catalyst | | Elapsed time [hour] | Specific surface area of catalyst [m²/g] | Adsorbed amount of ammonia per specific surface area of catalyst [μmol/m²] | Activity test | | |
|---|---|---|---|---|---|---|---|
| | | | | | Conversion ratio of propylene [%] | Acrylonitrile yield [%] | Ammonia combustion rate [%] |
| Comparative Example 2 | Fluidized bed catalyst 1 | 0 | 45 | 0.42 | — | — | — |
| | | 100 | 44 | 0.36 | 98.6 | 82.2 | 12.1 |
| | | 300 | 42 | 0.76 | 98.0 | 78.5 | 28.0 |

As can be seen from the results of Table 2, it was possible to produce acrylonitrile while maintaining a high acrylonitrile yield of 81% or more in the case of Examples 1 to 3 in which the vapor phase catalytic ammoxidation reaction was performed while maintaining the adsorbed amount of ammonia per specific surface area (m²/g) of the fluidized bed catalyst during the vapor phase catalytic ammoxidation process in the range of 0.05 to 0.6 μmol/m². It was possible to produce acrylonitrile while maintaining a higher acrylonitrile yield of 81.9% or more particularly in the case of Example 1 in which the vapor phase catalytic ammoxidation reaction was performed while maintaining the adsorbed amount of ammonia per specific surface area (m²/g) of the fluidized bed catalyst during the reaction in the range of 0.08 to 0.5 μmol/m². In addition, in the case of Examples 1 to 3, an attached substance derived from molybdenum was not confirmed on the inner wall or the like of the reactor after the reaction. Moreover, there was no change in the fluidized bed catalyst used.

On the other hand, in the case of Comparative Example 1, the yield of acrylonitrile decreased during the vapor phase catalytic ammoxidation reaction when the adsorbed amount of ammonia per specific surface area (m²/g) of the fluidized bed catalyst during the reaction was less than 0.05 mol/m². In addition, an attached substance derived from molybdenum was not confirmed on the inner wall or the like of the reactor after the reaction. Moreover, there was no change in the fluidized bed catalyst used.

In addition, in the case of Comparative Example 2, the yield of acrylonitrile decreased during the vapor phase catalytic ammoxidation reaction when the adsorbed amount of ammonia per specific surface area (m²/g) of the fluidized bed catalyst during the reaction was more than 0.6 μmol/m². In addition, a white attached substance derived from molybdenum was confirmed on the inner wall or the like of the reactor after the reaction. Moreover, the same white attached substance was confirmed on the fluidized bed catalyst used.

From these results, the acrylonitrile yield when the ammonia adsorption amount during the vapor phase catalytic ammoxidation process was in the range of 0.05 to 0.6 μmol/m² was higher than the yield when the ammonia adsorption amount was out of the above range. It was confirmed the relation of the ammonia adsorption amount and the yield of acrylonitrile, namely that a decrease in the yield of acrylonitrile can be effectively suppressed when the ammonia adsorption amount is within the above range.

Consequently, according to the invention, it is possible to suppress a time-dependent decrease in the acrylonitrile yield and to stably maintain a high acrylonitrile yield over a long period of time by performing the vapor phase catalytic ammoxidation reaction while maintaining the adsorbed amount of ammonia per specific surface area (m²/g) of the fluidized bed catalyst during the vapor phase catalytic ammoxidation process in the range of 0.05 to 0.6 μmol/m².

The invention claimed is:

1. A method for producing acrylonitrile, the method comprising
performing vapor phase catalytic ammoxidation by bringing a source gas comprising propylene, molecular oxygen, and ammonia into contact with a fluidized bed catalyst thereby obtaining acrylonitrile,
wherein the fluidized bed catalyst comprises molybdenum and bismuth, and
the vapor phase catalytic ammoxidation is performed while maintaining an adsorbed amount of ammonia per specific surface area (m²/g) of the fluidized bed catalyst in the range of from 0.05 to 0.6 μmol/m² throughout the entire vapor phase catalytic ammoxidation,
wherein the adsorbed amount of ammonia per specific surface area (m²/g) of the fluidized bed catalyst in the range of from 0.05 to 0.6 μmol/m² is maintained by increasing or decreasing the ammonia adsorption amount,
and wherein
the increasing of the amount of ammonia adsorbed is performed by adding a compound comprising an element which exhibits acidity in order to promote the adsorption of ammonia, and
the decreasing of the amount of ammonia adsorbed is performed by adding a compound comprising an element which exhibits basicity in order to inhibit the adsorption of ammonia.

2. The method for producing acrylonitrile according to claim 1, wherein the fluidized bed catalyst is represented by Formula (1):

$$Mo_{12}Bi_aFe_bA_cD_dE_eG_fO_x(SiO_2)_y \qquad (1)$$

wherein in Formula (1), Mo, Bi, Fe, O, and SiO₂ represent molybdenum, bismuth, iron, oxygen, and silica, respectively,
A represents at least one element selected from the group consisting of nickel, cobalt, zinc, magnesium, manganese, and copper,
D represents at least one element selected from the group consisting of lanthanum, cerium, praseodymium, neodymium, and samarium,
E represents at least one element selected from the group consisting of lithium, sodium, potassium, rubidium, and cesium,
G represents at least one element selected from the group consisting of calcium, strontium, barium, cadmium, titanium, zirconium, vanadium, niobium, tantalum, chromium, tungsten, germanium, tin, yttrium, aluminum, gallium, ruthenium, rhodium, palladium, rhenium, osmium, iridium, platinum, silver, boron, phosphorus, antimony, and tellurium, and
a, b, c, d, e, f, x, and y represent an atomic ratio, and a is from 0.1 to 5, b is from 0.1 to 10, c is from 2 to 12, d is from 0.01 to 5, e is from 0.01 to 2, f is from 0 to 10, y is from 20 to 200, and x is the number of oxygen atom required to satisfy the valence of each of the components except silica with the proviso that c, d, e and f represent a sum of an atomic ratio of each element in a case in which A, D, E and G contain two or more elements.

3. The method according to claim 1, wherein the vapor phase catalytic ammoxidation is done at a temperature of from 350 to 500° C.

4. The method according to claim 1, wherein the vapor phase catalytic ammoxidation is done at a pressure of from 100 to 500 kPa.

5. The method according to claim 1, wherein the source gas has a mole ratio of propylene:ammonia:oxygen in the range of from 1:1 to 2:1 to 5.0.

* * * * *